US010406299B2

(12) United States Patent
Seguin et al.

(10) Patent No.: US 10,406,299 B2
(45) Date of Patent: Sep. 10, 2019

(54) PHARMACEUTICAL COMPOSITION AND DEVICE FOR TREATING PAIN

(71) Applicant: VAPOMED LIMITED, Nassau (BS)

(72) Inventors: Jacques Seguin, Launen (CH); Emad Sabry, La Croix-sur-Lutry (CH)

(73) Assignee: Vapomed Limited, Nassau (BS)

( * ) Notice: Subject to any disclaimer, the term of this patent is extended or adjusted under 35 U.S.C. 154(b) by 287 days.

(21) Appl. No.: 15/120,120

(22) PCT Filed: Feb. 8, 2016

(86) PCT No.: PCT/EP2016/052640
§ 371 (c)(1),
(2) Date: Aug. 18, 2016

(87) PCT Pub. No.: WO2016/124788
PCT Pub. Date: Aug. 11, 2016

(65) Prior Publication Data
US 2017/0100333 A1 Apr. 13, 2017

(30) Foreign Application Priority Data

Feb. 6, 2015 (FR) ..................................... 15 50985

(51) Int. Cl.
*A61M 11/00* (2006.01)
*A61K 45/06* (2006.01)
(Continued)

(52) U.S. Cl.
CPC ............ *A61M 11/00* (2013.01); *A61K 9/0043* (2013.01); *A61K 9/0078* (2013.01);
(Continued)

(58) Field of Classification Search
CPC ............ A61M 11/00–08; A61M 15/08; A61M 2205/27; A61M 2205/276;
(Continued)

(56) References Cited

U.S. PATENT DOCUMENTS

| 4,464,378 A | 8/1984 | Hussain |
| 4,950,237 A | 8/1990 | Henault et al. |

(Continued)

FOREIGN PATENT DOCUMENTS

| CN | 102068697 B | 10/2013 |
| EP | 1 370 212 A1 | 12/2003 |

(Continued)

OTHER PUBLICATIONS

Database WPI, XP002751415, Thomson Scientific, London, GB; AN 2011-H53355, CN102068697 A (Yichang Humanwell Pharm Co Ltd) May 25, 2011, Abstract.

(Continued)

*Primary Examiner* — Kami A Bosworth
(74) *Attorney, Agent, or Firm* — Foley & Lardner LLP; Christopher C. Bolten; Nicola A. Pisano

(57) ABSTRACT

The invention relates to a system for the sequential intranasal administration of at least one active ingredient selected from a DR group having at least one side effect of respiratory depression and at least one active ingredient selected from an ADR group that counteracts the respiratory depression that may be induced by the active ingredients of the DR group. The invention also relates to a portable sequential intranasal administration device comprising an intranasal administration system according to the principles of the invention.

10 Claims, 2 Drawing Sheets

(51) Int. Cl.
    A61K 31/135    (2006.01)
    A61K 31/4535   (2006.01)
    A61K 31/485    (2006.01)
    A61K 31/5517   (2006.01)
    A61M 15/08     (2006.01)
    A61K 9/00      (2006.01)
    A61M 31/00     (2006.01)
    A61M 39/22     (2006.01)
    A61M 16/00     (2006.01)

(52) U.S. Cl.
    CPC ........ *A61K 31/135* (2013.01); *A61K 31/4535* (2013.01); *A61K 31/485* (2013.01); *A61K 31/5517* (2013.01); *A61K 45/06* (2013.01); *A61M 15/08* (2013.01); *A61M 31/00* (2013.01); *A61M 39/22* (2013.01); *A61M 2016/0021* (2013.01); *A61M 2205/33* (2013.01); *A61M 2205/3334* (2013.01); *A61M 2205/3569* (2013.01); *A61M 2205/50* (2013.01); *A61M 2205/52* (2013.01); *A61M 2205/583* (2013.01); *A61M 2205/587* (2013.01); *A61M 2205/8206* (2013.01); *A61M 2205/8256* (2013.01); *A61M 2205/8262* (2013.01); *A61M 2210/0618* (2013.01); *A61M 2230/005* (2013.01); *A61M 2230/20* (2013.01); *A61M 2230/205* (2013.01); *A61M 2230/42* (2013.01); *A61M 2230/435* (2013.01)

(58) Field of Classification Search
    CPC ...... A61M 2205/3303; A61M 2205/52; A61M 2210/0618; A61M 2230/005; A61M 2230/205; A61M 2230/42; A61M 2230/435; A61K 9/0043
    See application file for complete search history.

(56) References Cited

U.S. PATENT DOCUMENTS

| | | | |
|---|---|---|---|
| 4,969,579 A | 11/1990 | Behar | |
| 5,512,578 A | 4/1996 | Crain et al. | |
| 5,535,950 A | 7/1996 | Barriac et al. | |
| 5,629,011 A | 5/1997 | Illum | |
| 5,767,125 A | 6/1998 | Crain et al. | |
| 5,767,215 A | 6/1998 | Garoff et al. | |
| 6,098,620 A * | 8/2000 | Lloyd | A61M 15/00 128/200.14 |
| 6,605,060 B1 | 8/2003 | O'Neil | |
| 6,610,271 B2 | 8/2003 | Wermeling | |
| 6,948,492 B2 | 9/2005 | Wermeling et al. | |
| 7,875,001 B2 | 1/2011 | Minotti | |
| 8,198,291 B2 | 6/2012 | Wermeling | |
| 8,857,429 B2 | 10/2014 | Spandorfer | |
| 8,987,290 B2 | 3/2015 | Woodward | |
| 9,173,837 B2 | 11/2015 | Hillis et al. | |
| 2003/0077300 A1 | 4/2003 | Wermeling | |
| 2003/0191147 A1 | 10/2003 | Sherman et al. | |
| 2004/0068222 A1* | 4/2004 | Brian | A61M 11/06 604/65 |
| 2004/0115133 A1 | 6/2004 | Wermeling | |
| 2004/0129270 A1 | 7/2004 | Fishman | |
| 2005/0126562 A1* | 6/2005 | Rabinowitz | A61M 15/00 128/200.23 |
| 2006/0130828 A1* | 6/2006 | Sexton | A61M 15/00 128/200.14 |
| 2006/0207596 A1 | 9/2006 | Lane | |
| 2007/0043032 A1 | 2/2007 | Mainville | |
| 2007/0186923 A1 | 8/2007 | Poutiatine et al. | |
| 2010/0331354 A1 | 12/2010 | Wermeling | |
| 2012/0187937 A1 | 7/2012 | Blake et al. | |
| 2012/0270895 A1 | 10/2012 | Wermeling | |
| 2013/0090594 A1 | 4/2013 | Palmer et al. | |
| 2013/0172759 A1 | 7/2013 | Melker et al. | |
| 2014/0099369 A1 | 4/2014 | Oshlack et al. | |
| 2015/0000673 A1 | 1/2015 | Martin | |
| 2016/0354558 A1 | 12/2016 | Seguin et al. | |

FOREIGN PATENT DOCUMENTS

| | | |
|---|---|---|
| EP | 1 727 549 A1 | 12/2006 |
| WO | WO-96/40332 A1 | 12/1996 |
| WO | WO-01/58447 A1 | 8/2001 |
| WO | WO-2005/020906 A2 | 3/2005 |
| WO | WO-2008/027499 A2 | 3/2008 |
| WO | WO-2008/085765 A2 | 7/2008 |
| WO | WO-2009/021106 A1 | 2/2009 |
| WO | WO-2009/114740 A2 | 9/2009 |
| WO | WO-2012/024106 A2 | 2/2012 |
| WO | WO-2013/021186 A1 | 2/2013 |
| WO | WO-2016/124788 A1 | 8/2016 |

OTHER PUBLICATIONS

Helmers, et al., Comparison of Intra-Venous and Intranasal Sufentanil Absorption and Sedation, Canadian Journal of Anesthesia, pp. 494-497 (1989).

Lundeberg, et al., Aspects of Pharmacokinetics and Pharmacodynamics of Sufentanil in Pediatric Practice, Pediatric Anesthesia, (21):274-279 (2011).

Nielsen, et al., Intranasal Sufentanil/Ketamine Analgesia in Children, Pediatric Anesthesia, (2):170-80 (2014); (Abstract Only).

Intranasal Medications in the Prehospital Setting, Therapeutic Intranasal Drug Delivery, 2010, accessed Nov. 6, 2017, available at www.intranasal.net.

International Search Report & Written Opinion dated Mar. 24, 2016 in Int'l PCT Patent Application Serial No. PCT/EP2016/052640, with English translation (16 pages).

Wante, La voie intra nasale, available at https://www.chu-brugmann.be/fr/news/20121206-criticalday-wante.pdf, Dec. 6, 2012, accessed Nov. 6, 2017.

* cited by examiner

PHARMACEUTICAL COMPOSITION AND DEVICE FOR TREATING PAIN

CROSS-REFERENCE TO RELATED APPLICATIONS

This application is a national phase of International PCT Patent Application No. PCT/EP2016/052640, filed Feb. 8, 2016, which claims priority to FR Patent Application No. 1550985, filed Feb. 6, 2015, the entire contents of each of which are incorporated herein by reference.

BACKGROUND

The present invention relates to the field of pain management, including the field of pain management based on active ingredients that may have respiratory depressant side effects.

Among the active ingredients that may have respiratory depressant effects, the invention is specifically directed to opioid agonists and benzodiazepines.

Opioid agonists are substances whose effects are similar to opium, but not chemically related. Opioid agonists exert their effect by stimulation of opioid receptors. Complex formation opioid agonist/receptor causes a pharmacological response relative to the type of opioid receptor (also called opiate receptor).

Opioid agonists are used therapeutically for the treatment of pain, and are also used as a replacement during detox treatment.

A number of opioid agonists are commonly used. For example, a non-exhaustive list includes alfentanil, anileridine, apomorphine, buprenorphine, butorphanol, carfentanil, codeine, diamorphine ("Heroin"), dextropropoxyphene, dihydromorphine, fentanyl, hydrocodone, hydromorphone, levallorphan, levophenacylmorphan, levorphanol, methadone, morphine, nalbuphine, nalorphine, norlevophanol, oxycodone, oxymorphone, pentazocine, pethidine, propoxyphene, remifentanil, sufentanil, tramadol, etc.

In addition, a number of endogenous substances may be classified as opioid agonists: dynorphins, endorphins, endorphins, enkephalins, nociceptors, etc.

Opioid agonists may have many undesirable side effects including drowsiness, respiratory depression, constipation, nausea/vomiting, etc. Their use should be handled with care, especially in the hospital or any health care setting.

Treatment with opioid agonists pose many problems of misuse because they may be a substitute for hard drugs. Consequently, supply clinics require expensive security systems. Finally, the rapid addiction to this kind of treatment associated with long-term treatment resulting in increased doses may make the patient dependent, especially when the administration is "on demand." As a result, an opioid agonist-based therapy requires strict regulation and strong involvement of medical staff, which is problematic in the context of cost optimization.

There are three main types of opioid receptors, mu (μ), delta (δ) and kappa (κ). These receptors are widely distributed in the brain and in some peripheral areas.

Opioid antagonists, in contrast to opioid agonists, are characterized by an inhibitory activity of at least one opioid receptor. They may be divided into two main classes: the specific opioid antagonists and non-specific opioid antagonists. Among the non-specific opioid antagonists are, in particular, naloxone, naltrexone and nalmefene.

In the case of opioid poisoning, to limit certain side effects, opioid agonists may be associated with opioid antagonists.

For the administration of opioids, injectable solutions are predominantly used today, especially in the hospital environment. This form of administration has a number of advantages, for example, the effect is very fast and bioavailability is quite well controlled. However, administration by injection is not perfect. In fact, in addition to the discomfort of the injection and the requirement of a professional for administration, some side effects are very pronounced including, but not limited to respiratory depression.

Benzodiazepines are used primarily for their main properties: hypnotics, anxiolytics antiepileptics, muscle relaxant, and amnesic.

A number of benzodiazepines are commonly used. For example, a non-exhaustive list includes alprazolam, bromazepam, chlordiazepoxide, clobazam, clonazepam, clotiazepam, clorazepate, diazepam, estazolam, flunitrazepam, loprazolam, lorazepam, lormetazepam, midazolam, nitrazepam, nordazepam, oxazepam, prazepam, temazepam, tetrazepam, triazolam, etc.

Benzodiazepines have many undesirable side effects including amnesia, abnormal behavior, tolerance, respiratory depression, etc.

Benzodiazepine antagonists, unlike benzodiazepines, are characterized by an inhibitory activity of the activity of benzodiazepines. The best known benzodiazepine antagonists is flumazenil.

In the case of benzodiazepines intoxication, to limit certain side effects, e.g., respiratory depression, benzodiazepines may be associated with a benzodiazepine antagonist.

In the context of this application, the term "active ingredients from the DR group" refers to active ingredients with at least one side effect of respiratory depression.

In the context of this application, the term "active ingredients from the ADR group" refers to active ingredients that counter respiratory depression induced by the active ingredients of the DR group.

Opioid agonists and benzodiazepines, for example, are active ingredients of the DR group with at least one side effect of respiratory depression.

Opioid antagonists and benzodiazepine antagonists, for example, are active ingredients of the ADR group that counteract respiratory depression.

Unless otherwise defined, each technical or scientific term used herein has the sa: meaning as commonly understood by one of ordinary skill in the art to which this disclosure belongs. In accordance with the claims that follow and the disclosure provided herein, the following terms are defined with the following meanings, unless explicitly stated otherwise.

"Active Formulation" include a formulation comprising one or more active pharmaceutical ingredients. The active ingredients may be formulated as a solution in which non-molecular dispersion. The active ingredients may also be formulated in a form modifying its properties, particularly those related to the passage of membranes and bioavailability; microcapsules, liposomes, fast acting forms, etc.

"Intranasal administration" is the administration of the active ingredients in the patient's nasal cavity. The active ingredients may be in different forms: gas, steam, microdroplets, suspended powder, etc. In one embodiment, the active ingredients are in aerosol form, e.g., in a suspension of fine solid particles in a liquid or gas, wherein the particles fall under 50 cm per second. Intranasal administration is also characterized by the fact that most of the active ingredients are absorbed by the nasal mucosa of the patient.

"Sequential administration" is the administration of one or more successive administrations of the active ingredients.

"Respiratory depression" is a side effect following the administration of several active ingredients, e.g., hypoxia tissue, increased carbon dioxide levels in exhaled air, reduced oxygen levels in the exhaled air, decreased respiratory rate, decreased breathing amplitude, etc.

"Undesirable side effect" is the effect of an active ingredient that it is not directly desired. The undesirable side effect may be limited by administering an amount of the active ingredient that counteracts the undesirable side effect.

"Independent administration" is when the administration is performed by the patient himself or herself without the intervention of a health professional. When the administration takes place in animals, it is understood that the administration is carried out by the breeder.

"Energy Source" is an independent energy source which may be useful to permit the independent administration as indicated above. The energy source is generally portable, and preferably incorporated into a portable system of the intranasal delivery device. For example, the energy source may be a battery, a source of photovoltaic energy, energy recovered from the patient, e.g., heat generated by motion, etc.

"Administration without any medical facility" means that a sequence of one or more successive administrations may take place without any supervision of a health professional. Optionally, the therapy may be prescribed by a health professional, while the administration itself takes place in a place where such professionals are neither present nor necessary.

"Initial stage" is the time period during which the first administration of the therapy is performed.

"Subsequent stage" refers to the time period that any administration after the first administration of the therapy is performed.

"Administration simultaneously/simultaneous administration" is the administration of at least two active ingredients. Alternatively, each active ingredient may be administered such that their pharmacological effect begin at the same time and/or are generally simultaneous. In another aspect, the active ingredients may be formulated as a mixture.

"Choice of administration" is when the patient receives an administration because the patient wants to.

"Information means" is an element whose function is to acquire and transmit information for decision making, e.g., a choice of administration. It may be a time counting means for measuring at least one biological parameter.

"Time counting means" refers to any means of measuring time intervals. It may include a clock, a stopwatch, a countdown timer, a microprocessor operating at a known frequency operation, etc.

"Biological parameter" refers to a patient's biological characteristic, which is in the form of a numerical value where quantifiable. For example, it may be oxygen saturation or respiratory rate.

"Device for measuring at least one biological parameter" is a device that produces a numerical value corresponding to a biological parameter of the patient.

"Device for measuring at least one biological parameter introduced concomitantly" is a device where at least one portion is located in the nasal cavity during at least the beginning of the administration.

"Patient signal means" is an element that emits a signal perceptible to the patient, thereby allowing the patient to obtain information on the choice of the administration. The signal may be a light signal. When the signal is positive, it means that active formulation containing active ingredients from the DR group without active ingredients from the ADR group may be issued. When the signal is negative, it means that active formulation containing active ingredients from the ADR group, but no active ingredients of the DR group may be issued. For example, when at least one of the information means transmits information to the signal processing unit opposing the link between the active formulation containing active ingredients of the DR group without active ingredients of the ADR group and the dispensing means, then the patient signal means transmits a negative signal to the patient.

"Liquid spray" is liquid capable of being transformed into droplets and/or microdroplets.

"Mixture of active ingredients" is the presence of active ingredients within a single storage space. The mixture may be in liquid, solid, or gas. In the case of a gas mixture, molecules of different active ingredients may be dispersed within the same storage space called a molecular mixture.

"Opioid agonist" is an active ingredient which acts on at least one opioid receptor in a manner similar to opium.

"Opioid antagonist" is an active ingredient which acts on at least one opioid receptor inverse to opium.

"Initial actuation system" refers to the first operation of the administration of therapy achieved by the patient wishing, to receive an initial administration. There may only be one initial actuation system during a single therapy.

"Subsequent actuation system" refers to subsequent operation of the administration of therapy achieved by the patient wishing to receive an administration. There may be one or more subsequent actuation systems during a single therapy.

"Portable device for intranasal administration" is a device that may be carried by the patient, and not as a burden that limits its mobility. In particular, the device may be so easily transported that a mere possibility of having to use it, e.g., in an emergency, justifies its portability. It may be arranged in a pocket, a hand, a bag, a box car glove, a handbag, a capsule resistant to water and/or sand, etc.

"Storage space" is an enclosed space containing an active formulation. In the enclosed space, air exchange with the outside is low or nonexistent, and cannot, in the short run, cause a qualitative and/or quantitative formulation. During use, the enclosed space may communicate with the outside.

"Linking means" refers to all the elements allowing communication between the storage space and the dispensing means. It may in particular be a mechanical barrier, e.g., a valve.

"Signal processing unit" is an element related to both information means and linking means. Information means sends information that is evaluated by the signal processing unit. Operation of the signal processing unit allows the signal processing unit to issue operation control signals to the linking means based on the assessment made.

"Excessive respiratory depression" is a state of respiratory depression wherein the risk/benefit of simultaneous administration of at least one active ingredient of the DR group and at least one active ingredient of the ADR group is not desirable. For example, when the measured biological parameter is oxygen saturation, respiratory depression may be considered excessive when the oxygen saturation value is lower than 85° h. In addition, when the biological parameter is respiratory rate, respiratory depression may be considered excessive when the value of the respiratory rate is less than 12 cycles of inspiration/expiration per minute.

"Removable storage space" is storage space that may be removed from the device without making it permanently unusable.

"Changeable storage space" is storage space that may be acquired, according to the regulations in force, regardless of the device. The changeable storage space may be withdrawn and replaced with new storage spaces including, where appropriate, the same active ingredients in order to reload the device.

"Dispensing means suitable for transmission of active formulations through the nasal mucosa" is an element or set of elements needed to bring active formulations in contact with the nasal mucosa.

"Power source" is a supply of electric current to the portable device. This electric current may be generated by, for example, a battery, a capacitor, means of collecting solar energy, means for collecting the patient's energy, e.g., mechanical energy or body heat, etc.

Despite the strong need for therapy with analgesic active ingredients such as opioid agonists and benzodiazepines, that need is limited by side effects, particularly respiratory depression. In the future, these therapies will present a number of improvements:

From an ergonomics of treatment point of view: secure management made easier, noninvasive administration, limit post-treatment harm, etc.

From a financial point of view: limit the intervention of the nursing staff, reduce hospitalization durations, reduce misuse impacting health systems, reduce costs of distribution networks, etc.

From a public health point of view: reduce respiratory depression, limit misuse; etc.

In particular, there is a long felt need for a technical solution for delivering in an independent, controlled manner, by the patient himself without any medical facility, active ingredients used in the treatment of pain while at the same time managing the adverse side effects of such treatment. This need especially is especially felt by people, e.g., soldiers, journalists, adventurers, explorers, hunters, hikers, climbers, who are far from any medical personnel or treatment center, e.g., hospital, clinic, health center, etc. Indeed, these people are often found in places where the Objective dangers involving the maintenance of bodily integrity are quite significant, and the risk of inflicting traumatic injury is quite high. These people therefore need a single therapeutic solution enabling them to manage all kinds of situations where there is a manifestation of pain through proper administration of suitable products, while at the same time, avoid suffering from undesirable side effects.

Various efforts have been made to improve opioid therapy, but satisfactory results have yet to be obtained.

For example, Chinese application CN 102068697 describes combining an opioid agonist and an opioid antagonist in attempt to limit the adverse effects of the opioid agonist without impacting its effect. Specifically, the application teaches a nasal spray comprising a mixture of fentanyl/naltrexone. However, the application fails to describe limiting the number of administrations or any way of controlling the potential side effects once the opioid antagonist metabolizes.

U.S. Patent Pub. No. 2007/0186923, assigned to AcelRx Pharmaceuticals, describes a medical delivery device for the administration of opioid agonists in the oral mucosa. The device has a safety component which prevents opioid antagonist spill when attempting to recover the opioid agonist solution. The application is therefore a security system ensuring the neutralization of the effect of the opioid agonist composition in case of attempted hijacking, making the composition unusable. Under normal conditions, no mixing occurs between the opioid agonist and the opioid antagonist, and no antagonist administration takes place.

WO 2012024106, assigned to the University of Florida, describes a complex system consisting of acquisition of pharmacokinetic and pharmacodynamic data, algorithmic analysis, wherein the response may be variable. The application specifies that the oximeter is not considered a reliable device for detecting abnormality, and that other probes are preferred. In addition, the device is not transportable.

WO 1996040332, assigned to Go Medical, describes a medical device for intranasal administration of an opioid agonist. The device comprises an opioid agonist solution and other active molecules other than opioid antagonists, thus no opioid antagonist incorporation is envisaged. The application fails to describe limiting misuse, and only describes a control system wherein a patient uses "good faith."

U.S. Pat. No. 4,464,378 describes methods of intranasal administration of antagonists and corresponding formulations, for example, in gel form. The objective expressed in this patent is to circumvent the difficulties encountered with the use of certain known products which showed insufficient bioavailability during oral administration. This patent describes formulating solutions, gels, suspensions, and ointments containing the opioid agonist-antagonist for intranasal administration.

U.S. Pat. No. 5,629,011 describes intranasal formulations of polar metabolites of opioid agonists in combination with an absorption promoter acting in the raucous membranes.

U.S. Pat. No. 5,767,125 describes a method of co-administration of an opioid agonist with an opioid antagonist. The opioid agonist is selected from morphine, codeine, fentanyl analogs, pentazocine, buprenorphine, methadone, enkephalins, dynorphins, endorphins, and alkaloids and opioid peptides which behave in the same way. The opioid antagonist is selected from naltrexone, naloxone, etorphine, diprenorphine, dihydroetorphine, and alkaloids and opioid peptides behaving in the same way. The product is administered to mice by intraperitoneal injection, but the patent raises the possibility of preparing formulations for oral, sublingual, intravenous, intramuscular, subcutaneous, and transdermal administration.

WO 2001058447 describes compositions containing an opioid agonist and an opioid antagonist that may be formulated for intranasal administration. It should be noted that here the opioid antagonist is coated with a substrate, e.g., a polysaccharide, to form microspheres to control its release on the mucous membranes so as to ensure the effect of the opioid antagonist during the effect.

U.S. Pat. No. 6,948,492 describes systems and intranasal delivery devices regarding controlling the minimum time between intranasal self-administration of a plurality of unit doses of a pharmaceutical composition. Unit doses contained in bottles are deposited on a support star around a hub that may rotate to advance the unit dosage after each use, but only after a certain predetermined time has elapsed. The support star is biased constantly to rotate and advance the bottles, the progression of which is retained by a metal spring and a shape memory alloy wire. The locking is controlled by a microprocessor which counts down between each administration. This patent does not describe co-administering an opioid agonist and an opioid antagonist, or another form of control preventing the inappropriate administration of the composition. Indeed, although it is possible for the disclosed device to self-administer subsequent doses of opioid composition, the dosage is not in a physiological condition to withstand such administration.

In summary, none of the solutions mentioned above resolve all the problems described above.

As will be discussed below, a device in accordance with the present invention solves the problems mentioned above.

SUMMARY

The present invention relates to uses, systems, devices incorporating such systems, and methods of administration, for managing pain. The various aspects of the invention will be described in further detail below.

The implementation of the present invention will have advantages:

Regarding the ergonomics of treatment: secure management made easier, noninvasive administration, limit post-treatment harm, etc.

Regarding the financial aspect: limit the intervention of the nursing staff, reduce hospitalization durations, reduce misuse impacting health systems, reduce costs of distribution networks, etc.

From the public health point of view: reduce respiratory depression, limit misuse, etc.

The present invention also relates to uses, systems, devices incorporating such systems, and methods of administration, for managing pain in animals. Regarding the methods of administration, it is understood that the administration is performed by the master/breeder of the animal and not the animal patient/subject.

The present invention relates to a method of sequential intranasal administration of at least one active ingredient from the DR group with at least one side effect of respiratory depression, and at least one active ingredient of the ADR group that counteracts the respiratory depression that may be induced by the active ingredients of the DR group. The method may be implemented by the patient independently without any medical facility and comprises:

An initial stage of intranasal administration of at least one active ingredient from the DR group, and At least one subsequent stage of intranasal administration of at least one active ingredient from the ADR group alone or in combination with at least one active ingredient from the DR group, wherein the choice of the administration of the at least one subsequent stage of intranasal administration is controlled by one or more information means.

In one embodiment, the sequential intranasal administration method comprises:

An initial stage of intranasal administration of at least one active ingredient from the DR group in combination with at least one active ingredient from the ADR group, and At least one subsequent stage of intranasal administration of at least one active ingredient from the ADR group alone or of at least one active ingredient from the DR group and at least one active ingredient from the ADR group simultaneously, wherein the choice of the administration of the at least one subsequent stage of intranasal administration is controlled by one or more information means.

In one embodiment, the initial stage of the sequential intranasal administration method further comprises administering at least one active ingredient from the ADR group simultaneously with that of the at least one active ingredient from the DR group.

In one embodiment, when at least one active ingredient from the DR group is an opioid, and at least one active ingredient from the ADR group is an active ingredient that counteracts the opioid-induced respiratory depression, e.g., naloxone, it will be expected that when the opioid from the DR group is administered, the active ingredient, e.g., naloxone, of the ADR group may be administered simultaneously.

In one embodiment, when at least one active ingredient from the DR group is a benzodiazepine, and at least one active ingredient from the ADR Group is an active ingredient that counteracts the benzodiazepine-induced respiratory depression, e.g., flumazenil, it will be expected that when the benzodiazepine of the DR group is administered, the active ingredient, e.g., flumazenil, of the ADR group may be administered simultaneously.

In one embodiment, the sequential intranasal administration method comprises:

An initial stage of intranasal administration of at least one active ingredient from the DR group, and At least one subsequent stage of intranasal administration of at least one active ingredient solely from the ADR group, wherein the choice of the administration of the at least one subsequent stage of intranasal administration is controlled by one or more information means.

In one embodiment, the sequential intranasal administration method comprises:

An initial stage of intranasal administration of at least one active ingredient from the DR group, and At least one subsequent stage of intranasal administration of at least one active ingredient from the DR group and at least one active ingredient from the ADR group simultaneously, wherein the choice of the administration of the at least one subsequent stage of intranasal administration is controlled by one or more information means.

In one embodiment, the sequential intranasal administration method comprises:

An initial stage of intranasal administration of at least one active ingredient from the DR group and at least one active ingredient from the ADR group, and At least one subsequent stage of intranasal administration of at least one active ingredient from the ADR group alone, wherein the choice of the administration of the at least one subsequent stage of intranasal administration is controlled by one or more information means.

In one embodiment, the sequential intranasal administration method comprises:

An initial stage of intranasal administration of at least one active ingredient from the DR group and at least one active ingredient from the ADR group, and At least one subsequent stage of intranasal administration of at least one active ingredient from the DR group and at least one active ingredient from the ADR group simultaneously, wherein the choice of the administration of the at least one subsequent stage of intranasal administration is controlled by one or more information means.

In one embodiment, the initial stage is also controlled by one or more means of information.

In one embodiment, at least one active ingredient from the DR group and at least one active ingredient from the ADR group, when administered simultaneously, are in a mixture.

In one embodiment, the information means is at least one measuring device, at least one biological parameter, and/or a time counting means.

In one embodiment, the information means is at least one measuring device, at least one biological parameter, and a time counting means.

In one embodiment, the information means is at least one oximeter, and/or a respiration rate sensor, and/or a time counting means.

In one embodiment, the information means is at least one oximeter, a respiratory rate sensor, and a time counting means.

In one embodiment:
When the time counting means indicates a dosage interval lower than a threshold value, the subsequent stage of intranasal administration involves the administration of at least one active ingredient from the ADR group;
AND/OR
When at least one device for measuring at least one biological parameter indicates excessive respiratory depression, the subsequent stage of intranasal administration involves the administration of at least one active ingredient from the ADR group;
AND
In all other cases, the subsequent stage of intranasal administration involves the administration of at least one active ingredient from the DR group.

In one embodiment:
When the time counting means indicates a dosage interval lower than a threshold value, the subsequent stage of intranasal administration involves the administration of at least one active ingredient from the ADR group;
AND/OR
When at least one device for measuring at least one biological parameter indicates excessive respiratory depression, the subsequent stage of intranasal administration involves the administration of at least one active ingredient from the ADR group;
AND
In all other cases, the subsequent stage of intranasal administration involves the administration of at least one active ingredient from the DR group and at least one active ingredient from the ADR group simultaneously.

The present invention also provides the use of at least one active ingredient from the DR group having at least one side effect of respiratory depression and at least one active ingredient from the ADR group that counteracts respiratory depression induced by the active ingredients of the DR group, for the treatment of pain. The use may be part of a sequential intranasal administration implemented by the patient himself without any medical facility, wherein the sequential intranasal administration includes:
An initial stage of intranasal administration of at least one active ingredient from the DR group, and
At least one subsequent stage of intranasal administration of at least one active ingredient from the ADR group alone or in combination at least one active ingredient from the DR group,
wherein the choice of the administration of the at least one subsequent stage of intranasal administration is controlled by one or more information means.

The present invention also provides a method for the intranasal administration of an active ingredient from the DR group having a side effect of respiratory depression for treating pain, characterized in that it is administered together sequentially with at least one active ingredient from the ADR group that counteracts the respiratory depression induced by the active ingredient from the DR group. The method of intranasal administration may be implemented independently, outside of any medical facility, and comprises:
An initial stage of intranasal administration of at least one active ingredient from the DR group, and
At least one subsequent stage of intranasal administration of at least one active ingredient from the ADR group alone or in combination with at least one active ingredient from the DR group,
wherein the choice of the administration of the at least one subsequent stage of intranasal administration is controlled by one or more information means.

In one embodiment, the active ingredients for use in a method of treatment of pain are characterized in that at least one active ingredient from the DR group is benzodiazepine, and at least one active ingredient from the ADR group is flumazenil.

In one embodiment, the active ingredients for use in a method of treatment of pain are characterized in that at least one active ingredient from the DR group is sufentanil, and at least one active ingredient from the ADR group is naloxone.

In one embodiment, when at least one active ingredient from the DR group is an opioid, and at least one active ingredient from the ADR group is an active ingredient that counteracts the opioid-induced respiratory depression, e.g., naloxone, it will be expected that when the opioid from the DR group is administered, the active ingredient from the ADR group, e.g., naloxone, may be administered simultaneously.

In one embodiment, when at least one active ingredient from the DR group is a benzodiazepine, and at least one active ingredient from the ADR group is an active ingredient that counteracts the benzodiazepine-induced respiratory depression, e.g., flumazenil, it will be expected that when the benzodiazepine from the DR group is administered, the active ingredient from the ADR group, e.g., flumazenil, may be administered simultaneously.

In one embodiment, the active ingredient from the DR group with at least one side effect of respiratory depression for use in a method of treating pain, is characterized in that it is sequentially administered intranasally with at least one active ingredient from the ADR group that counteracts the respiratory depression induced by the active ingredients of the DR group. The method of intranasal administration may be implemented independently, outside of any medical facility, and comprises:
An initial stage of intranasal administration of at least one active ingredient from the DR group and at least one active ingredient from the ADR group, and
At least one subsequent stage of intranasal administration of at least one active ingredient from the ADR group alone or of at least one active ingredient from the DR group and at least one active ingredient from the ADR group simultaneously,
wherein the choice of the administration of the at least one subsequent stage of intranasal administration is controlled by one or more information means.

In one embodiment, the active ingredient from the DR group with at least one side effect of respiratory depression for use in a method of treating pain, is characterized in that it is sequentially administered intranasally with at least one active ingredient from the ADR group that counteracts the respiratory depression induced by the active ingredients of the DR group. The method of intranasal administration may be implemented independently, outside of any medical facility, and comprises:

An initial stage of intranasal administration of at least one active ingredient from the DR group, and At least one subsequent stage of intranasal administration of at least one active ingredient from the ADR group alone, wherein the choice of the administration of the at least one subsequent stage of intranasal administration is controlled by one or more information means.

In one embodiment, the method of administration dosage comprises:

An initial stage of intranasal administration of at least one active ingredient from the DR group, and At least one subsequent stage of intranasal administration of at least one active ingredient from the DR group and at least one active ingredient from the ADR group simultaneously, wherein the choice of the administration of the at least one subsequent stage of intranasal administration is controlled by one or more information means.

In one embodiment, the method of administration dosage comprises:

An initial stage of intranasal administration of at least one active ingredient from the DR group and at least one active ingredient from the ADR group, and At least one subsequent stage of intranasal administration of at least one active ingredient from the ADR group alone, wherein the choice of the administration of the at least one subsequent stage of intranasal administration is controlled by one or more information means.

In one embodiment, the method of administration dosage comprises:

An initial stage of intranasal administration of at least one active ingredient from the DR group and at least one active ingredient from the ADR group, and At least one subsequent stage of intranasal administration of at least one active ingredient from the DR group and at least one active ingredient from the ADR group simultaneously, wherein the choice of the administration of the at least one subsequent stage of intranasal administration is controlled by one or more information means.

In one embodiment, the initial stage is also controlled by one or more information means.

In one embodiment, at least one active ingredient from the DR group and at least one active ingredient from the ADR group, when administered simultaneously, are in a mixture.

In one embodiment, the information means is at least one measuring device, at least one biological parameter and/or a time counting means.

In one embodiment, the information means is at least one measuring device, at least one biological parameter, and a time counting means.

In one embodiment, the information means is at least one oximeter and/or a respiration rate sensor and/or a time counting means.

In one embodiment, the information means is at least one oximeter, a respiratory rate sensor, and a time counting means.

In one embodiment:

When the time counting means indicates a dosage interval lower than a threshold value, the subsequent stage of intranasal administration involves the administration of at least one active ingredient from the ADR group;

AND/OR

When at least one device for measuring at least one biological parameter indicates excessive respiratory depression; the subsequent stage of intranasal administration involves the administration of at least one active ingredient from the ADR group;

AND

In all other cases, the subsequent stage of intranasal administration involves the administration of at least one active ingredient from the DR group.

In one embodiment:

When the time counting means indicates a dosage interval lower than a threshold value, the subsequent stage of intranasal administration involves the administration of at least one active ingredient from the ADR group;

AND/OR

When at least one device for measuring at least one biological parameter indicates excessive respiratory depression, the subsequent stage of intranasal administration involves the administration of at least one active ingredient from the ADR group;

AND

In all other cases, the subsequent stage of intranasal administration involves the administration of at least one active ingredient from the DR group and at least one active ingredient from the ADR group simultaneously.

In one embodiment, the sequential intranasal administration implemented by the patient himself; without any medical facility comprises:

An initial stage of intranasal administration of at least one active ingredient from the DR group and at least one active ingredient from the ADR group, and At least one subsequent stage of intranasal administration of at least one active ingredient from the ADR group alone, or of at least one active ingredient from the DR group and at least one active ingredient from the ADR group simultaneously, wherein the choice of the administration of the at least one subsequent stage of intranasal administration is controlled by one or more information means.

In one embodiment, the at least one active ingredient from the DR group and the at least one active ingredient from the ADR group, when administered simultaneously, are in a mixture.

In one embodiment, when at least one active ingredient from the DR group is an opioid, and at least one active ingredient from the ADR group is an active ingredient that counteracts the opioid-induced respiratory depression, e.g., naloxone, the opioid from the DR group is administered simultaneously with the active ingredient from the ADR group, e.g., naloxone.

In one embodiment, the at least one active ingredient from the DR group and the at least one active ingredient from the ADR group, when administered simultaneously, are in a mixture.

In one embodiment, when at least one active ingredient from the DR group is a benzodiazepine, and at least one active ingredient from the ADR group is an active ingredient that counteracts the benzodiazepine-induced respiratory depression, e.g., flumazenil, the benzodiazepine from the DR group is administered simultaneously with the active ingredient from the ADR group, e.g., flumazenil.

In one embodiment, the sequential intranasal administration implemented by the patient himself, without any medical facility includes:

An initial stage of intranasal administration of at least one active ingredient from the DR group, and At least one subsequent stage of intranasal administration of at least one active ingredient from the ADR group alone, wherein the choice of the administration of the at least one subsequent stage of intranasal administration is controlled by one or more information in cans.

In one embodiment, the sequential intranasal administration implemented by the patient himself, without any medical facility includes:

An initial stage of intranasal administration of at least one active ingredient from the DR group, and At least one subsequent stage of intranasal administration of at least one active ingredient from the DR group, wherein the choice of the administration of the at least one subsequent stage of intranasal administration is controlled by one or more information means.

In one embodiment, the intranasal sequential administration implemented by the patient himself, without any medical facility includes:

An initial stage of intranasal administration of at least one active ingredient from the DR group and at least one active ingredient from the ADR group, and At least one subsequent stage of intranasal administration of at least one active ingredient from the ADR group alone, wherein the choice of the administration of the at least one subsequent stage of intranasal administration is controlled by one or more information means.

In one embodiment, the sequential intranasal administration implemented by the patient himself, without any medical facility includes:

An initial stage of intranasal administration of at least one active ingredient from the DR group and at least one active ingredient from the ADR group, and At least one subsequent stage of intranasal administration of at least one active ingredient from the DR group and at least one active ingredient from the ADR group simultaneously, wherein the choice of the administration of the at least one subsequent stage of intranasal administration is controlled by one or more information means.

In one embodiment, the initial stage is also controlled by a number of information means.

In one embodiment, the information means is at least one measuring device, at least one biological parameter, and/or a time counting means.

In one embodiment, the information means is at least one measuring device, at least one biological parameter, and a time counting means.

In one embodiment, the information means is at least one oximeter, and/or a respiration rate sensor, and/or a time counting means.

In one embodiment, the information means is at least an oximeter, a respiratory rate sensor, and a time counting means.

In one embodiment:

When the time counting means indicates a dosage interval lower than a threshold value, the subsequent stage of intranasal administration involves the administration of at least one active ingredient from the ADR group;

AND/OR

When at least one device for measuring at least one biological parameter indicates excessive respiratory depression, the subsequent stage of intranasal administration involves the administration of at least one active ingredient from the ADR group;

AND

In all other cases, the subsequent stage of intranasal administration involves the administration of at least one active ingredient from the DR group.

In one embodiment:

When the time counting means indicates a dosage interval lower than a threshold value, the subsequent stage of intranasal administration involves the administration of at least one active ingredient from the ADR group;

AND/OR

When at least one device for measuring at least one biological parameter indicates excessive respiratory depression, the subsequent stage of intranasal administration involves the administration of at least one active ingredient from the ADR group;

AND

In all other cases, the subsequent stage of intranasal administration involves the administration of at least one active ingredient from the DR group and at least one active ingredient from the ADR group simultaneously.

The invention also relates to a sequential intranasal administration system.

This administration system may be particularly useful for isolated people in situations similar to those mentioned above.

In particular, the invention relates to a system for sequential intranasal administration of at least one active ingredient from the DR group with at least one side effect of respiratory depression and at least one active ingredient from the ADR group that counteracts the respiratory depression induced by the active ingredients of the DR group. The system comprises:

(A) simultaneous administration of at least one active ingredient from the DR group in response to an initial operation of the system made by a patient wishing to receive pharmaceutical administration, this administration constituting an initial administration recorded by the system;

(B) at least one subsequent administration to the initial administration of at least one active ingredient from the ADR group or at least one active ingredient from the DR group, in response to at least one subsequent operation of the system made by the patient wishing to receive the subsequent pharmaceutical administration, this administration constituting a subsequent event recorded by the system;

wherein the choice of the subsequent administration is controlled by one or more information means.

In one embodiment, the system includes:

(A) simultaneous administration of at least one active ingredient from the DR group and at least one active ingredient from the ADR group in response to an initial operation of the system made by a patient wishing to receive pharmaceutical administration, this administration constituting an initial administration recorded by the system;

(B) at least one subsequent administration to the initial administration of at least one active ingredient from the ADR group, or at least one active ingredient from the DR group and at least one active ingredient from the ADR group simultaneously, in response to at least one subsequent operation of the system performed by the patient wishing to receive the subsequent pharmaceutical administration, this administration constituting a subsequent event recorded by the system;

wherein the choice of the subsequent administration is controlled by one or more information means.

In one embodiment, at least one active ingredient from the DR group and at least one active ingredient from the ADR group, when administered simultaneously, are in a mixture.

In one embodiment, when at least one active ingredient from the DR group is an opioid, and at least one active ingredient from the ADR group is an active ingredient that counteracts the opioid-induced respiratory depression, e.g., naloxone, the opioid of the DR group may be administered simultaneously with the active ingredient from the ADR group, e.g., naloxone.

In one embodiment, when at least one active ingredient from the DR group is a benzodiazepine, and at least one active ingredient from the ADR group is an active ingredient that counteracts the benzodiazepine-induced respiratory depression, e.g., flumazenil, the benzodiazepine of the DR group may be administered simultaneously with the active ingredient from the ADR group, e.g., flumazenil.

In one embodiment, the system includes:
  An initial intranasal administration of at least one active ingredient from the DR group, and
  At least one subsequent intranasal administration to the initial administration of at least one active ingredient from the ADR group alone,
wherein the choice of the subsequent intranasal administration is controlled by one or more information means.

In one embodiment, the system includes:
  An initial intranasal administration of at least one active ingredient from the DR group, and
  At least one subsequent intranasal administration of at least one active ingredient from the DR group,
wherein the choice of the subsequent intranasal administration is controlled by one or more information means.

In one embodiment, the system includes:
  An initial intranasal administration of at least one active ingredient from the DR group and at least one active ingredient from the ADR group, and
  At least one subsequent intranasal administration to the initial administration of at least one active ingredient from the ADR group alone,
wherein the choice of the subsequent intranasal administration is controlled by one or more information means.

In one embodiment, the system includes:
  An initial intranasal administration of at least one active ingredient from the DR group and at least one active ingredient from the ADR group, and
  At least one subsequent intranasal administration of at least one active ingredient from the DR group and at least one active ingredient from the ADR group simultaneously,
wherein the choice of the subsequent administration is controlled by one or more information means.

In one embodiment, the administration is a controlled by one or more information means including at least the measurement of a biological parameter.

In one embodiment, the information means is at least one measuring device, at least one biological parameter, and/or a time counting means.

In one embodiment, the information means is at least one measuring device, at least one biological parameter, and a time counting means.

In one embodiment, the information means is at least one oximeter, and/or a respiration rate sensor, and/or a time counting means.

In one embodiment, the information means is at least an oximeter, a respiratory rate sensor, and a time counting means.

In one embodiment:
  When the timer indicates a dosage interval lower than a threshold value, the subsequent administration comprises administering at least one active ingredient from the ADR group;
  AND/OR
  When at least one device for measuring at least one biological parameter indicates excessive respiratory depression, the subsequent administration comprises administering at least one active ingredient from the ADR group;
  AND
  In all other cases, the subsequent administration comprises administering at least one active ingredient from the DR group.

In one embodiment:
  When the timer indicates a dosage interval lower than a threshold value, the subsequent administration comprises administering at least one active ingredient from the ADR group;
  AND/OR
  When at least one device for measuring at least one biological parameter indicates excessive respiratory depression, the subsequent administration comprises administering at least one active ingredient from the ADR group;
  AND
  In all other cases, the subsequent administration comprises administering at least one active ingredient from the DR group and at least one active ingredient from the ADR group simultaneously.

The invention also relates to an intranasal administration system having a portable device for sequential intranasal administration in accordance with the present disclosure.

In one embodiment, the intranasal administration system having a portable device for sequential intranasal administration in accordance with the present disclosure includes:
  At least a first storage space containing a first active sprayable formulation comprising at least one active ingredient from the DR group;
  At least a second storage space containing a second active sprayable formulation different from the first active formulation comprising at least one active ingredient from the ADR group;
  A signal processing unit;
  Linking means of the first and second storage spaces having the first and second active formulations, respectively, and the dispensing means, operatively connected to the signal processing unit;
  One or more information means operably coupled to the signal processing unit;
  Control means allowing the patient to receive the active formulations by self-administration without any medical facility;
  Dispensing means for transmission of the active formulations through the nasal mucosa; and
  An autonomous power source,
wherein the signal processing unit, the linking means, the information means, and the control means are configured to allow, based on one or more signals received by the signal processing unit from the information means, the linking of the first active formulation within the first storage space to dispensing means or the linking of the second active formulation within the second storage space to the dispensing means.

In one embodiment, the intranasal administration system having a portable device for sequential intranasal administration in accordance with the present disclosure includes:

At least a first storage space containing a first active sprayable formulation comprising at least one active ingredient from the DR group and at least one active ingredient from the ADR group, mixed;

At least a second storage space with a second active sprayable formulation different from the first active formulation comprising at least one active ingredient from the ADR group;

A signal processing unit;

Linking means of the first and second active formulations of the first and second storage spaces, respectively, and the dispensing means, operatively connected to the signal processing unit;

One or more information means operably connected to the signal processing unit;

Control means al lowing the patient to receive the active formulations by self-administration without any medical facility;

Distribution means for transmission of the active formulations through the nasal mucosa; and An autonomous power source, wherein the signal processing unit in relation to the setting means, the information means and the control means are configured to allow, based on one or more signals received by the signal processing unit from the information means, the linking of the first active formulation within the first storage space to dispensing means or the linking second active formulation within the second storage space to the dispensing means.

When at least one active ingredient from the DR group is an opioid, and at least one active ingredient from the ADR group is an active ingredient that counteracts the opioid-induced respiratory depression, e.g., naloxone, the first storage space having the first active formulation disposed therein may include both an active ingredient from the DR group selected from opioids and an active ingredient from the ADR group, e.g., naloxone.

In one embodiment, at least one active ingredient from the DR group and at least one active ingredient from the ADR group, when administered simultaneously, are in a mixture.

When at least one active ingredient from the DR group is a benzodiazepine, and at least one active ingredient from the ADR group is an active ingredient that counteracts the benzodiazepine-induced respiratory depression, e.g., flumazenil, the first storage space having the first active formulation disposed therein may include both an active ingredient from the DR group selected from benzodiazepines and an active ingredient from the ADR group, e.g., flumazenil.

In one embodiment, the energy source is electric.

In one embodiment, the signal processing unit comprises a microprocessor.

In one embodiment, the signal processing unit is operatively connected to one or more memory areas configured to store data received from the information means.

In one embodiment, the information means is at least one measuring device, at least one biological parameter, and/or a time counting means.

In one embodiment, the information means is at least one device for measuring at least one biological parameter, and a time counting means.

In one embodiment, the information means is at least one oximeter, and/or a respiration rate sensor, and/or a time counting means.

In one embodiment, the information means is at least an oximeter, a respiratory rate sensor, and a time counting means.

In one embodiment, the dispensing means of the active formulation is a nosepiece, and the oximeter and respiratory rate sensor are located on the nosepiece for measuring and/or calculating a physiological value of the patient receiving the active formulation.

In one embodiment, the time counting means is integrated into the microprocessor of the signal processing unit.

In one embodiment:

The device for measuring and/or calculating at least one biological parameter sends information to the signal processing unit having a memory area configured to store the physiological value;

The signal processing unit, when receiving information from the device for measuring at least one biological parameter, interrogates the time counting means to obtain a current time value and stores the time value in a memory area.

In one embodiment:

The signal processing unit performs a comparison between the physiological value obtained from the device for measuring at least one biological parameter, and a threshold value stored in a memory area;

The signal processing unit performs a comparison between the time value stored in the memory area and an updated time value received from the time counting means at the time of the comparison to calculate an elapsed time interval since the previous administration;

Depending on the determination of these comparisons, the signal processing unit sends a signal to the linking means to allow the patient receiving the administration of the active formulation to actuate the control means and self-administer one of the active formulations.

In one embodiment:

If the signal processing unit determines that the physiological value is greater than a threshold value, and a sufficient time interval has elapsed since the previous administration, the signal processing unit sends a signal to the linking means to enable subsequent administration of the first active formulation; or If the signal processing unit determines that the physiological value is less than the threshold value, or an insufficient time interval has elapsed since the previous administration, the signal processing unit sends a signal to the linking means to enable subsequent administration of the second active formulation.

In one embodiment, the storage spaces are removable.

In one embodiment, the storage spaces are changeable. The storage spaces are "changeable" in that they may be removed and replaced with new storage spaces including, where appropriate, the same active ingredients.

In one embodiment, the storage spaces are removable and changeable.

Indeed, as stated above, the medical device may incorporate multiple active formulations, the qualitative and quantitative compositions of each of which may be adapted for a given patient. The choice of dosage as well as which active ingredients to use may be at the discretion of a medical personnel. In addition, the time interval may be predetermined by the medical personnel.

In one embodiment, the medical device further includes a patient signal means.

In one embodiment, the patient signal means is a light signal.

The invention will be better understood on reading the description of the figures which follows.

DETAILED DESCRIPTION

Figure 1:
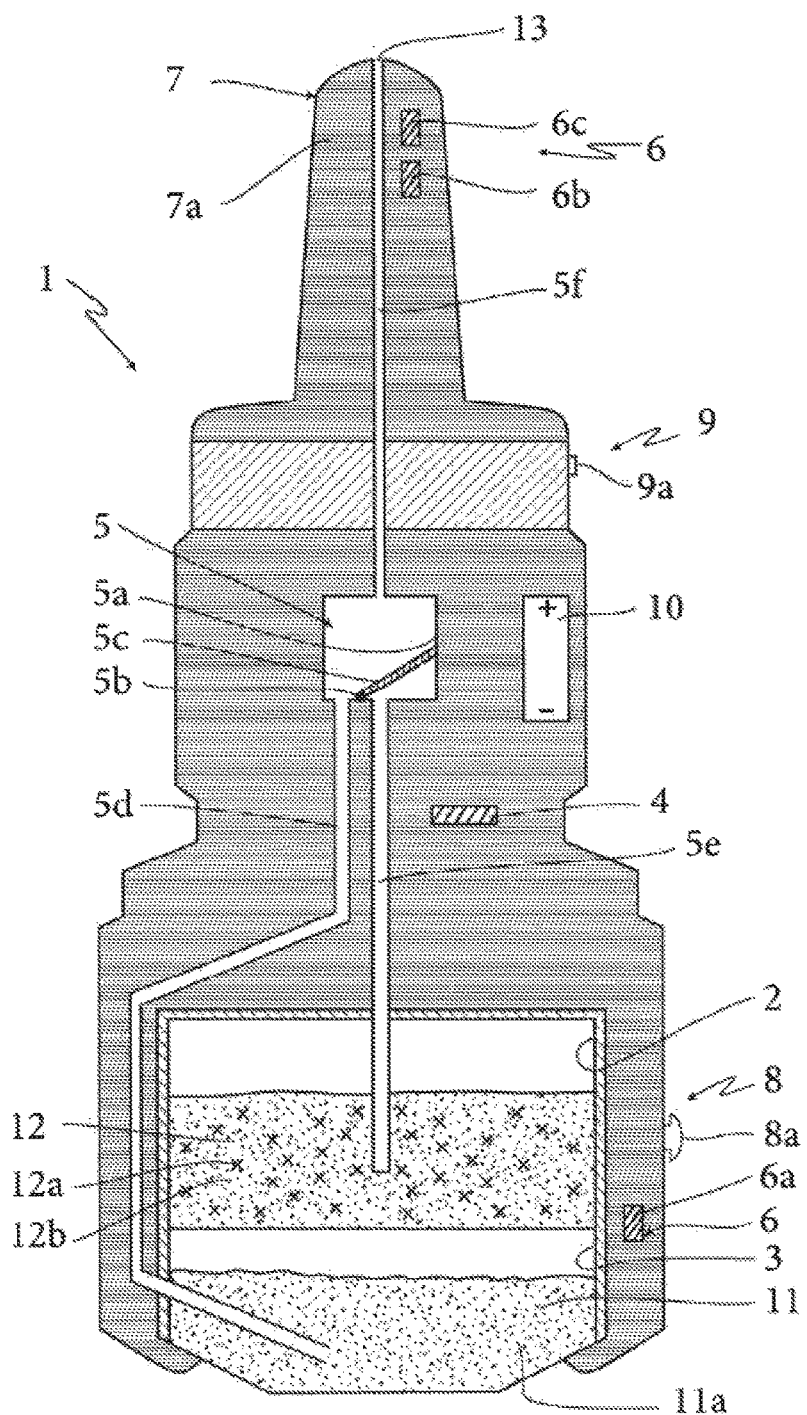
FIG. 1 illustrates an exemplary embodiment of a portable device for sequential intranasal administration in accordance with the principles of the present invention.

FIG. 1: example device according to the invention

FIG. 1 illustrates portable device 1 for intranasal administration in according with the principles of the present disclosure. First storage space 2 may contain first active formulation 12 comprising active ingredient from the DR group 12a and active ingredient from the ADR group 12b. Second storage space 3 may contain second active formulation 11 comprising at least one active ingredient from the ADR group 11a.

Signal processing unit 4 may be connected to linking means 5. Linking means 5 comprises dosage chamber 5a, valve Sc having valve shaft 5b, and ducts 5d and 5e connected to first and second storage spaces 3 and 2 respectively. Signal processing unit 4 may also be connected to information means 6. Information means 6 may comprise clock 6a, respiratory rate sensor 6b, and/or oximeter 6c.

When using device 1, the user inserts nosepiece 7a into the nasal cavity of the patient. Information means, for example oximeter 6c and/or respiratory rate sensor 6b, may measure and determine values, and communicate the values to signal processing unit 4. Signal processing unit 4 may also communicate with 6a clock to calculate the time elapsed since the last administration of active formulation 12. Alternatively, signal processing unit 4 may have a clock, e.g., a PSTN circuit, or other timer integrated therewith to avoid providing a separate clock.

When the user activates control means 8, illustrated in FIG. 1 as push button 8a, signal processing unit 4, based on information provided by information means 6, controls linking via linking means 5 of either first storage space 2 or second storage space 3 with dispensing means 7, e.g., nosepiece 7a, specifically through dispensing duct 5f.

As shown in FIG. 1, linking comprises actuating valve Sc mounted on valve shaft 5b inside dosage chamber 5a. Valve Sc may switch to either side of valve shaft 5b to be pressed against a side wall of dosage chamber 5a, and thus may close one of ducts 5d or 5e based on the active formulation to be administered as determined by signal processing unit 4.

The active formulation selected to be administered from device 1 flows through dispensing duct 5f and exits from outlet 13 before being brought into contact with the nasal mucosa.

At any time, the user may obtain information about the active formulation administered from activating pushbutton 8a through patient signal means 9, e.g., light 9a.

The user may then decide whether to activate push button 8a.

Device 1 may include autonomous power source 10. Autonomous power source 10 supplies power to device 1; and may be a rechargeable battery, photovoltaic cells; or other suitable source.

Figure 2:
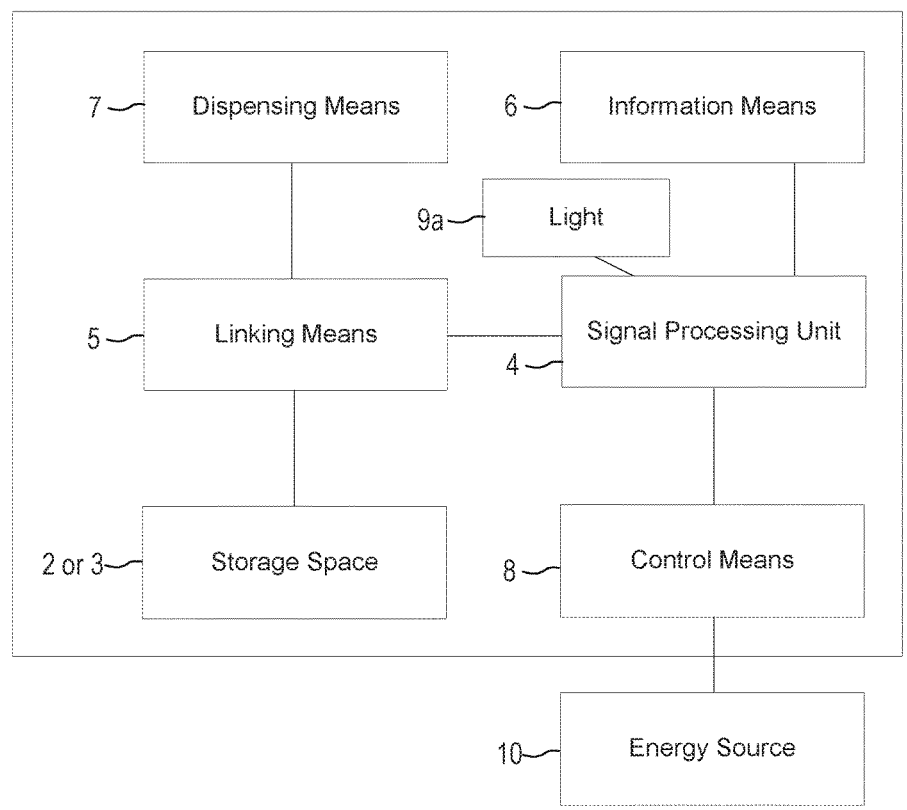
FIG. 2 is an exemplary embodiment of a schematic block diagram illustrating various features of the device of FIG. 1 in accordance with the principles of the present invention.

FIG. 2: functional diagram of a device according to the invention

FIG. 2 is a schematic block diagram illustrating various features of device 1 in accordance with the principles of the present disclosure.

FIG. 2 illustrates that signal processing unit 4 is connected to:
  information means 6;
  linking means 5;
  control means 8; and
  light 9a
  Linking means 5 is further connected to:
  first and second storage spaces 2 and 3;
  dispensing means 7.

When using device 1, information means 6 provides information to signal processing unit 4.

When the user activates control means 8, signal processing unit 4, based on the information provided by information means 6, controls linking via linking means 5 of either first storage space 2 or second storage space 3 with the dispensing means 7.

Autonomous power source 10 supplies power to device 1, and may be a rechargeable battery; photovoltaic cells, or other suitable source.

Device 1 may be used by a patient wishing to carry out the intranasal administration therapy. Device 1 may likely be used by people who are in isolated situations described above. To use device 1, the patient may quickly retrieve device 1 from, for example, a backpack, or its optional case. The user then positions dispensing means 7, e.g., nosepiece 7a. Patient signal means 9, e.g., light 9a, may communicate to the patient which of the two active formulations would be administered upon the activation of control means 8. Finally, to use device 1, the patient activates control means 8, e.g., pushbutton 8a. Control means 8 may also be any device capable of receiving a mechanical stress, voice activated, etc. The patient may, as part of the therapy, perform as many intranasal administrations as desired. Although this therapy may be an "on demand" therapy, it is completely safe and secure.

Device 1 may incorporate multiple active formulations, e.g., active formulations 11 and 12, the qualitative and quantitative compositions of each of which may be adapted for a given patient. The choice of dosage as well as which active ingredients to use may be at the discretion of a medical personnel. The time interval, e.g., minimum duration between administrations of active ingredients from the DR and/or ADR groups, calculated by the time counting means, e.g., clock 6a, may be predetermined by the medical personnel.

Accordingly, device 1 may simplify difficult situations, especially in the context of use during armed conflict, natural disasters, etc.

In one embodiment, intranasal delivery system having portable device 1 for sequential intranasal administration in accordance with the principles of the present disclosure includes:
  at least first storage space 2 containing first sprayable active formulation 12 comprising at least one active ingredient from the DR group 12a;
  at least second storage space 3 containing second sprayable active formulation 11 different from first active formulation 12 comprising at least one active ingredient from the ADR group 11a;
  signal processing unit 4;
  linking means 5 of active formulations 12 and 11 of first and second storage spaces 2 and 3, respectively, and dispensing means 7, operatively connected to signal processing unit 4;

one or more information means 6, operatively connected to signal processing unit 4;
control means 8 configured to allow a patient receiving active formulations to perform self-administration of the active formulations without any medical facility;
dispensing means 7 for transmission of the active formulations through the nasal mucosa; and
autonomous power source 10, wherein signal processing unit 4, linking means 5, information means 6, and control means 8 are configured to allow, based on one or more signals received by signal processing unit 4 from information means 6, linking of first active formulation 12 within first storage space 2 with dispensing means 7 and/or linking of second active formulation 11 within second storage space 3 with distribution means 7.

In one embodiment, intranasal delivery system having portable device 1 for sequential intranasal administration in accordance with the principles of the present disclosure includes:
at least first storage space 2 containing a first sprayable active formulation 12 comprising at least one active ingredient from the DR group 12a and at least one active ingredient from the ADR group 12b;
At least second storage space 3 comprising a second active formulation 11 sprayable different from first active formulation 12 comprising at least one active ingredient from the ADR group 11a;
signal processing unit 4;
linking means 5 of active formulations 12 and 11 of first and second storage spaces 2 and 3, respectively, and dispensing means 7, operatively connected to signal processing unit 4;
one or more information means 6, operatively connected to signal processing unit 4;
control means 8 configured to allow a patient receiving active formulations to perform self-administration of the active formulations without any medical facility;
dispensing means 7 for transmission of the active formulations through the nasal mucosa; and
autonomous power source 10, wherein signal processing unit 4, linking means 5, information means 6, and control means 8 are configured to allow, based on one or more signals received by signal processing unit 4 from information means 6, linking of first active formulation 12 within first storage space 2 with dispensing means 7 and/or linking of second active formulation 11 within second storage space 3 with distribution means 7.

In one embodiment, when at least one active ingredient from the DR group is an opioid, and at least one active ingredient from the ADR group is an active ingredient that counteracts the opioid-induced respiratory depression, e.g., naloxone, first storage space 2 having first active formulation 12 disposed therein may include both an active ingredient from the DR group selected from opioids and an active ingredient from the ADR group, e.g., naloxone.

In one embodiment, when at least one active ingredient from the DR group is a benzodiazepine, and at least one active ingredient from the ADR group is an active ingredient that counteracts the benzodiazepine-induced respiratory depression, e.g., flumazenil, first storage space 2 having first active formulation 12 disposed therein may include both an active ingredient from the DR group selected from benzodiazepines and an active ingredient from the ADR group, e.g., flumazenil.

In one embodiment, energy source 10 is electric.

In one embodiment, signal processing unit 4 comprises a microprocessor.

In one embodiment, signal processing unit 4 is operatively connected to one or more memory areas configured to store data received from information means 6.

In one embodiment, information means 6 includes at least one device for measuring at least one biological parameter, and/or a time counting means.

In one embodiment, information means 6 includes at least one device for measuring at least one biological parameter, and a time counting means.

In one embodiment, information means 6 includes at least one oximeter 6c, and/or respiratory rate sensor 6b, and/or time counting means.

In one embodiment, information means 6 includes at least one oximeter 6c, respiratory rate sensor 6b, and a time counting means.

In one embodiment, dispensing means 7 comprises nosepiece 7a, such that oximeter 6c and respiratory rate sensor 6b are located on nosepiece 6a for measuring and/or calculating a physiological value of the patient receiving the administration of active formulations.

In one embodiment, the time counting means is integrated in the microprocessor of signal processing unit 4.

In one embodiment:
the one or more devices for measuring and/or calculating at least one biological parameter sends the information to signal processing unit 4 having a memory area configured to store the physiological value; and
signal processing unit 4, upon receiving information from the device for measuring at least one biological parameter, interrogates the time counting means to obtain a current time value and stores the time value in a memory area.

In one embodiment:
signal processing unit 4 performs a comparison between a physiological value obtained from the one or more devices for measuring at least one biological parameter with a threshold value stored in a memory area;
signal processing unit 4 performs a comparison between the time value stored in a memory area and an updated time value received from the time counting means at the time of the comparison to calculate the time elapsed since the previous administration;
depending on the determination of these comparisons, signal processing unit 4 sends a signal to linking means 5 to enable the patient receiving the administration to actuate control means 8 to self-administer one of the active formulations.

In one embodiment:
if signal processing unit 4 determines that the physiological value exceeds a threshold value, and that sufficient time has elapsed since the previous administration, signal processing unit 4 sends a signal to linking means 5 to permit subsequent administration of first active formulation 12; or
if signal processing unit 4 determines that the physiological value is less than a threshold value, where an insufficient time interval has elapsed since the previous administration, signal processing unit 4 sends a signal to linking means 5 to permit subsequent administration of second active formulation 11.

In one embodiment, the storage spaces are removable.

In one embodiment, the storage spaces are changeable. The storage spaces are "changeable" in that they may be removed and replaced with new storage spaces including, where appropriate, the same active ingredients In one embodiment, storage spaces 2 and 3 are removable and changeable.

Indeed, as stated above, device 1 may include multiple active formulations, the qualitative and quantitative compositions of each of which may be adapted to a given patient. The choice of dosage as well as which active ingredients to use may be at the discretion of a medical personnel. In addition, the time interval may be predetermined by the medical personnel.

In one embodiment, device 1 further includes patient signal means 9.

In one embodiment; patient signal means 9 may be light 9a.

With respect to the doses of active ingredients from the DR and ADR group, all doses were estimated for patients of about 70 kg, which represents an average weight. Such doses may vary, especially for patients of different weights. The doses may also be adapted for specific animals. The doses may be adjusted as is well known in the art.

The following embodiments may be applied to the method of administration of the active ingredients for use in the treatment of pain, the administration system, and the portable device in accordance with the principles of the present disclosure.

In one embodiment, the measurement of a biological parameter is obtained by a device for measuring at least one biological parameter introduced into the nasal cavity concomitantly with each administration.

In one embodiment, the threshold value of the time counting means is between 1 and 10 hours.

In one embodiment, the threshold value of the time counting means is between 4 and 8 hours.

In one embodiment, the threshold value of the time counting means is about 6 hours.

In one embodiment, the biological parameter measured is selected from at least one of oxygen saturation, intranasal rate of oxygen exhaled, intranasal rate of carbon dioxide exhaled, or respiratory rate.

In one embodiment, the biological parameter measured is oxygen saturation.

In one embodiment, the threshold value of the measurement of the oxygen saturation is between 70 and 90%.

In one embodiment, the threshold value of the measurement of the oxygen saturation is between 80 and 90%.

In one embodiment, the threshold value of the measurement of oxygen saturation is about 85%.

In one embodiment, the biological parameter measured is respiratory rate.

In one embodiment, the threshold value of the measured respiratory rate is between 8 and 14 cycles/minute.

In one embodiment, the threshold value of the measured respiratory rate is between 8 and 12 cycles/minute.

In one embodiment, the threshold value of measuring respiratory rate is about 12 cycles/minute.

In one embodiment, the biological parameters measured are oxygen saturation and respiratory rate.

In one embodiment, the active ingredients are in the form of sprayable liquid.

In one embodiment, at least one active ingredient from the DR group and at least one active ingredient from the ADR group, when administered simultaneously, are in a mixture.

In one embodiment, only one active ingredient from the DR group and only one active ingredient from the ADR group are used.

In one embodiment, the active ingredients from the DR group used during the initial stage and the active ingredients from the DR group used during at least one subsequent stage are identical.

In one embodiment, the active ingredients from the DR group used during the initial stage and the active ingredients from the DR group used during at least one subsequent stage are different.

In one embodiment, the active ingredients from the ADR group used during the initial stage and the active ingredients from the ADR group used during at least one subsequent stage are identical.

In one embodiment, the active ingredients from the ADR group used during the initial stage and the active ingredients from the ADR group used during at least one subsequent stage are different.

In one embodiment, the active ingredients from the DR group consists of opioid agonists and the active ingredients from the ADR group consists of opioid antagonists.

In one embodiment, at least one active ingredient from the DR group is selected from the group consisting of alfentanil, anileridine, apomorphine, buprenorphine, butorphanol, carfentanil, codeine, diamorphine ("Heroin"), dextropropoxyphene, dihydromorphine, fentanyl, hydrocodone, hydromorphone, levallorphan, levophenacylmorphan, levorphanol, methadone, morphine, nalbuphine, nalorphine, norlevophanol, oxycodone, oxymorphone, pentazocine, pethidine, propoxyphene, remifentanil, sufentanil, tramadol, etc.

In one embodiment, at least one active ingredient from the DR group is selected from the group consisting of sufentanil, fentanyl, diamorphine, buprenorphine, and carfentanil.

In one embodiment, at least one active ingredient from the DR group is sufentanil, In one embodiment, at least one active ingredient from the ADR group is selected from the group consisting of naloxone and naltrexone.

In one embodiment, at least one active ingredient of the ADR group is naloxone.

In one embodiment, at least one active ingredient from the DR group is sufentanil and at least one active ingredient from the ADR group is naloxone.

In one embodiment, the dose of sufentanil is between 2 and 50 μg and the dose of naloxone is between 2 and 50 mg.

In one embodiment, the dose of sufentanil is between 5 and 30 μg and the dose of naloxone is between 5 and 30 mg.

In one embodiment, the dose of sufentanil is between 10 and 20 μg and the dose of naloxone is between 10 and 20 mg.

In one embodiment, the dose of sufentanil is 10 μg and the dose of naloxone is 10 mg.

In one embodiment, the dose of sufentanil is 15 μg and the dose of naloxone is 15 mg.

In one embodiment, the dose of sufentanil is 20 μg and the dose of naloxone is 20 mg.

In one embodiment, the weight ratio of sufentanil and naloxone is between 0.00004 and 0.025.

In one embodiment, the weight ratio of sufentanil and naloxone is about 0.001.

In one embodiment, at least one active ingredient of the DR group is sufentanil and at least one active ingredient of the ADR group is naloxone, and any administration of sufentanil is accompanied by the simultaneous administration of ketamine.

In one embodiment, sufentanil, naloxone, and ketamine are in a mixture.

In one embodiment, the dose of sufentanil is between 1 and 60 μg, the dose of ketamine is between 1 and 60 mg, and the dose of naloxone is between 1 and 60 mg.

In one embodiment, the dose of sufentanil is between 10 and 55 μg, the dose of ketamine is between 10 and 55 mg, and the dose of naloxone is between 10 and 55 mg.

In one embodiment, the dose of sufentanil is between 17 and 50 µg, the dose of ketamine is between 17 and 50 mg, and the dose of naloxone is between 17 and 50 mg.

In one embodiment, the dose of sufentanil is 17 µg, the dose of ketamine is 17 mg, and the dose of naloxone is 17 mg.

In one embodiment, the dose of sufentanil dose is 37.5 µg, the dose of ketamine is 37.5 mg, and the dose of naloxone is 37.5 mg.

In one embodiment, the dose of sufentanil dose is 50 µg, the dose of ketamine is 50 mg, and the dose of naloxone is 50 mg.

In one embodiment, the weight ratio of sufentanil and naloxone and the weight ratio of ketamine and naloxone are, respectively, between 0.00034 and 0.0029, and between 0.34 and 2.9.

In one embodiment, the weight ratio of sufentanil and naloxone ratio is about 0.001 and the weight ratio of ketamine and naloxone ratio is about 1.

In one embodiment, at least one active ingredient from the DR group is fentanyl and at least one active ingredient from the ADR group is naloxone.

In one embodiment, the dose of fentanyl is between 10 and 150 g and the dose of naloxone is between 2 and 50 mg.

In one embodiment, the dose of fentanyl is between 30 and 120 µg and the dose of naloxone is between 5 and 30 mg.

In one embodiment, the dose of fentanyl is between 50 and 100 µg and the dose of naloxone is between 10 and 20 mg.

In one embodiment, the dose of fentanyl is 50 µg and the dose of naloxone is 10 mg.

In one embodiment, the dose of fentanyl is 75 µg and the dose of naloxone is 15 mg.

In one embodiment, the dose of fentanyl is 100 µg and the dose of naloxone is 20 mg.

In one embodiment, the weight ratio of fentanyl and naloxone is between 0.0002 and 0.075.

In one embodiment, the weight ratio of fentanyl and naloxone ratio is about 0.005.

In one embodiment, at least one active ingredient from the DR group is diamorphine and at least one active ingredient from the ADR group is naloxone.

In one embodiment, the dose of diamorphine is between 0.1 and 20 mg and the dose of naloxone is between 2 and 50 mg.

In one embodiment, the dose of diamorphine is between 1 and 10 mg and the dose of naloxone is between 5 and 30 mg.

In one embodiment, the dose of diamorphine is between 2 and 4 mg and the dose of naloxone is between 10 and 20 mg.

In one embodiment, the dose of diamorphine is 2 mg and the dose of naloxone is 10 mg.

In one embodiment, the dose of diamorphine is 3 mg and the dose of naloxone is 15 mg.

In one embodiment, the dose of diamorphine is 4 mg and the dose of naloxone is 20 mg.

In one embodiment, the weight ratio of diamorphine and naloxone is between 0.02 and 10.

In one embodiment, the weight ratio of diamorphine and naloxone is about 0.2.

In one embodiment, at least one active ingredient from the DR group is buprenorphine and at least one active ingredient from the ADR group is naloxone.

In one embodiment, the dose of buprenorphine is between 0.1 and 30 mg and the dose of naloxone is between 0.1 and 5 mg.

In one embodiment, the dose of buprenorphine is between 1 and 15 mg and the dose of naloxone is between 0.3 and 3 mg.

In one embodiment, the dose of buprenorphine is between 2 and 8 mg and the dose of naloxone is between 0.5 and 2 mg.

In one embodiment, the dose of buprenorphine is 2 mg and the dose of naloxone is 0.5 mg.

In one embodiment, the dose of buprenorphine is 4 mg and the dose of naloxone is 1 mg.

In one embodiment, the dose of buprenorphine is 6 mg and the dose of naloxone is 1.5 mg.

In one embodiment, the dose of buprenorphine is 8 mg and the dose of naloxone is 2 mg.

In one embodiment, the weight ratio of buprenorphine and naloxone is between 0.02 and 300.

In one embodiment, the weight ratio of buprenorphine and naloxone is about 4.

In one embodiment, at least one active ingredient from the DR group is carfentanil and at least one active ingredient from the ADR group is naloxone.

In one embodiment, the dose of carfentanil dose is between 70 and 1900 µg and the dose of naloxone is between 0.3 and 3.7 mg.

In one embodiment, the dose of carfentanil dose is between 140 and 1400 µg and the dose of naloxone is between 0.5 and 3.0 mg.

In one embodiment, the dose of carfentanil dose is between 350 and 1000 µg and the dose of naloxone is between 0.7 and 2.0 mg.

In one embodiment, the dose of carfentanil dose is 350 µg and the dose of naloxone is 0.70 mg.

In one embodiment, the dose of carfentanil dose is 700 µg and the dose of naloxone is 1.4 mg.

In one embodiment, the dose of carfentanil dose is 1000 µg and the dose of naloxone is 2 mg.

In one embodiment, the weight ratio of carfentanil and naloxone is between 0.019 and 6.6.

In one embodiment, the weight ratio of carfentanil and naloxone is about 0.5.

In one embodiment, when the active formulation contains no active ingredient from the DR group, at least one active ingredient from the ADR group is naloxone and the dose of naloxone is between 1 and 40 mg.

In one embodiment, when the active formulation contains no active ingredient from the DR group, at least one active ingredient from the ADR group is naloxone and the dose of naloxone is between 5 and 20 mg.

When the at least one active ingredient from the DR group is buprenorphine and the active formulation contains no active ingredient from the DR group, at least one active ingredient from the ADR group is naloxone and the dose of naloxone is between 3 to 7 mg.

In one embodiment, the DR group consists of benzodiazepines and the ADR group consists of benzodiazepines antagonists.

In one embodiment, benzodiazepines are selected from the group consisting of lorazepam, midazolam and flunitrazepam.

In one embodiment, the benzodiazepine antagonist s flumazenil.

In one embodiment, the benzodiazepine is lorazepam and the benzodiazepine antagonist is flumazenil.

In one embodiment, the dose of lorazepam is between 2 and 5 mg.

In one embodiment, the benzodiazepine is midazolam and the benzodiazepine antagonist is flumazenil.

In one embodiment, the dose of midazolam is between 3.5 and 10 mg.

In one embodiment, the benzodiazepine is flunitrazepam and the benzodiazepine antagonist is flumazenil.

In one embodiment, the dose of flunitrazepam is between 2 and 10 mg.

In one embodiment, the active formulation contains no active ingredient from the DR group, at least one active ingredient from the ADR group is flumazenil, and the dose of flumazenil is between 0.1 and 1 mg.

In one embodiment, when the active formulation contains no active ingredient from the DR group, at least one active ingredient from the ADR group is flumazenil and the dose of flumazenil is between 0.6 and 1 mg.

In one embodiment, when the active formulation contains at least one active ingredient from the DR group and no active ingredient from the ADR group, at least one active ingredient from the DR group is selected from benzodiazepines.

In one embodiment, when at least one active ingredient from the DR group is lorazepam, the active formulation containing lorazepam does not include flumazenil.

In one embodiment, when at least one active ingredient from the DR group is midazolam, the active formulation containing midazolam does not include flumazenil.

In one embodiment, when at least one active ingredient from the ADR group is flunitrazepam, the active formulation containing flunitrazepam does not include flumazenil.

In one embodiment, the active ingredient from the DR group consists of opioid agonist and the active ingredient from the ADR group consists of opioid antagonists, and when at least one active ingredient from the DR group is administered, it is simultaneously administered with an active ingredient from the ADR group.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, at least one active ingredient from the DR group and at least one active ingredient from the ADR group, when administered simultaneously, are in a mixture, the active ingredient from the DR group used during the initial stage and the active ingredient from the DR group used during the at least one subsequent stage are identical, at least one active ingredient from the DR group is sufentanil, and at least one active ingredient from the ADR group is naloxone, wherein the dose of sufentanil is between 17 and 50 μg and the dose of naloxone is between 17 and 50 mg.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, at least one active ingredient from the DR group and at least one active ingredient from the ADR group, when administered simultaneously, are in a mixture, the active ingredient from the DR group used during the initial stage and the active ingredient from the DR group used during the at least one subsequent stage are identical, at least one active ingredient from the DR group is sufentanil, at least one active ingredient from the ADR group is naloxone, the dose of sufentanil is between 17 and 50 μg and the dose of naloxone is between 17 and 50 mg, any administration of sufentanil is accompanied by a simultaneous administration of ketamine, wherein the sufentanil and ketamine are in a mixture, and the dose of ketamine is between 17 and 50 mg.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, at least one active ingredient from the DR group and at least one active ingredient from the ADR group, when administered simultaneously, are in a mixture, the active ingredient from the DR group used during the initial stage and the active ingredient from the DR group used during the at least one subsequent stage are identical, at least one active ingredient from the DR group is fentanyl, and at least one active ingredient from the ADR group is naloxone, wherein the dose of fentanyl is between 50 and 100 μg and the dose of naloxone is between 10 and 20 mg.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, at least one active ingredient from the DR group and at least one active ingredient from the ADR group, when administered simultaneously, are in a mixture, the active ingredient from the DR group used during the initial stage and the active ingredient from the DR group used during the at least one subsequent stage are identical, at least one active ingredient from the DR group is diamorphine, and at least one active ingredient from the ADR group is naloxone, wherein the dose of diamorphine is between 2 and 4 mg and the dose of naloxone is between 10 and 20 mg.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, at least one active ingredient from the DR group and at least one active ingredient from the ADR group, when administered simultaneously, are in a mixture, the active ingredient from the DR group used during the initial stage and the active ingredient from the DR group used during the at least one subsequent stage are identical, at least one active ingredient from the DR group is buprenorphine, and at least one active ingredient from the ADR group is naloxone, wherein the dose of buprenorphine is between 2 and 8 mg and the dose of naloxone is between 0.5 and 2 mg.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, at least one active ingredient from the DR group and at least one active ingredient from the ADR group, when administered simultaneously, are in a mixture, the active ingredient from the DR group used during the initial stage and the active ingredient from the DR group used during the at least one subsequent stage are identical, at least one active ingredient from the DR group is carfentanil, and at least one active ingredient from the ADR group is naloxone, wherein the dose of carfentanil is between 350 and 1000 μg and the dose of naloxone is between 0.7 and 2.0 mg.

In one embodiment, the active ingredients from the DR group consists of opioid agonist and the active ingredients of the ADR group consists of opioid antagonists, and when at least one active ingredient from the DR group is administered, no active ingredient from the ADR group is administered.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, the active ingredient from the DR group used during the initial stage and the active ingredient from the DR group used during the at least one subsequent stage are identical, at least one active ingredient from the DR group is sufentanil, and at least one active ingredient from the ADR group is naloxone, wherein the dose of sufentanil is between 17 and 50 μg and the dose of naloxone is between 17 and 50 mg.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, the active ingredient from the DR group used during the initial stage and the active ingredient from the DR group used during the at least one subsequent stage are identical, at least one active ingredient from the DR group is sufentanil, at least one active ingredient from the ADR group is naloxone, the dose of sufentanil is between 17 and 50 μg and the dose of naloxone is between 17 and 50 mg, any administration of sufentanil is accompanied by a simultaneous administration of ketamine, wherein the sufentanil and ketamine are in a mixture, and the dose of ketamine is between 17 and 50 mg.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, the active ingredient from the DR group used during the initial stage and the active ingredient from the DR group used during the at least one subsequent stage are identical, at least one active ingredient from the DR group is fentanyl, and at least one active ingredient from the ADR group is naloxone, wherein the dose of fentanyl is between 50 and 100 μg and the dose of naloxone is between 10 and 20 mg.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, the active ingredient from the DR group used during the initial stage and the active ingredient from the DR group used during the at least one subsequent stage are identical, at least one active ingredient from the DR group is diamorphine, and at least one active ingredient from the ADR group is naloxone, wherein the dose of diamorphine is between 2 and 4 mg and the dose of naloxone is between 10 and 20 mg.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, the active ingredient from the DR group used during the initial stage and the active ingredient from the DR group used during the at least one subsequent stage are identical, at least one active ingredient from the DR group is buprenorphine, and at least one active ingredient from the ADR group is naloxone, wherein the dose of buprenorphine is between 2 and 8 mg and the dose of naloxone is between 0.5 and 2 mg.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, the active ingredient from the DR group used during the initial stage and the active ingredient from the DR group used during the at least one subsequent stage are identical, at least one active ingredient from the DR group is carfentanil, and at least one active ingredient from the ADR group is naloxone, wherein the dose of carfentanil is between 350 and 1000 μg and the dose of naloxone is between 0.7 and 2.0 mg.

In one embodiment, the active ingredients from the DR group consists of benzodiazepines and active ingredients from the ADR group consists of benzodiazepine antagonists, and when at least one active ingredient from the DR group is administered, an active ingredient from the ADR group is administered simultaneously.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, at least one active ingredient from the DR group and at least one active ingredient from the ADR group, when administered simultaneously, are in a mixture, the active ingredient from the DR group used during the initial stage and the active ingredient from the DR group used during the at least one subsequent stage are identical, at least one active ingredient from the DR group is midazolam, wherein the dose of midazolam is between 3.5 and 10 mg, and when the active formulation contains no active ingredient from the DR group, at least one active ingredient from the ADR group is flumazenil, wherein the dose of flumazenil is between 0.6 and 1 mg.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, at least one active ingredient from the DR group and at least one active ingredient from the ADR group, when administered simultaneously, are in a mixture, the active ingredient from the DR group used during the initial stage and the active ingredient from the DR group used during the at least one subsequent stage are identical, at least one active ingredient from the DR group is lorazepam, wherein the dose of lorazepam is between 2 and 5 mg, and when the active formulation contains no active ingredient from the DR group, at least one active ingredient from the ADR group is flumazenil, wherein the dose of flumazenil is between 0.6 and 1 mg.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, at least one active ingredient from the DR group and at least one active ingredient from the ADR group, when administered simultaneously, are in a mixture, the active ingredient from the DR group used during the initial stage and the active ingredient from the DR group used during the at least one subsequent stage are identical, at least one active ingredient from the DR group is flunitrazepam, wherein the dose of flunitrazepam is between 2 and 10 mg, and when the active formulation contains no active ingredient from the DR group, at least one active ingredient from the ADR group is flumazenil, wherein the dose of flumazenil is between 0.6 and 1 mg.

In one embodiment, the active ingredient from the DR group consists of benzodiazepines and the active ingredient from the ADR group consists of benzodiazepine antagonists, and when at least one active ingredient from the DR group is administered, no active ingredient from the ADR group is administered.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, the active ingredient from the DR group used during the initial stage and the active ingredient from the DR group used during the at least one subsequent stage are identical, at least one active ingredient from the DR group is midazolam, wherein the dose of midazolam is between 3.5 and 10 mg, and when the active formulation contains no active ingredient from the DR group, at least one active ingredient from the ADR group is flumazenil, wherein the dose of flumazenil is between 0.6 and 1 mg.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, the active ingredient from the DR group used during the initial stage and the active ingredient from the DR group used during the at least one subsequent stage are identical, at least one active ingredient from the DR group is lorazepam, wherein the dose of lorazepam is between 2 and 5 mg, and when the active formulation contains no active ingredient from the DR group, at least one active ingredient from the ADR group is flumazenil, wherein the dose of flumazenil is between 0.6 and 1 mg.

In one embodiment, the biological parameter is measured by a device for measuring at least one biological parameter introduced into the nasal cavity concomitantly with each administration, the threshold value of the time counting means is between 4 and 8 hours, the biological parameters measured are oxygen saturation and respiratory rate, the active ingredient from the DR group used during the initial stage and the active ingredient from the DR group used during the at least one subsequent stage are identical, at least one active ingredient from the DR group is flunitrazepam, wherein the dose of flunitrazepam is between 2 and 10 mg, and when the active formulation contains no active ingredient from the DR group, at least one active ingredient from the ADR group is flumazenil, wherein the dose of flumazenil is between 0.6 and 1 mg.

In one embodiment, at least one of the active formulations comprises at least one active pharmaceutical ingredient configured to modify the passage properties of membranes and bioavailability.

EXAMPLE

This example illustrates a use of device 1 in accordance with the principles of the present disclosure.

Specifications of device 1:
two removable storage spaces;
first storage space 2 having first active formulation 12 disposed therein: t,?

The amount of active formulation used in each dose is 0.2 mL, thus active formulation 12 comprises about 50 doses: sufentanil (37.5 µg/dose)/ketamine (37.5 mg/dose)/naloxone (37.5 mg/dose).

second storage space 3 comprises active formulation 11: t,?

The amount of active formulation used in each dose is 0.2 mL, thus active formulation 11 comprises about 50 doses: naloxone (15 mg/dose).

two devices that measure biological parameters: 6c oximeter (measuring oxygen saturation having 85% threshold value) and respiratory rate sensor 6b (threshold value: 12 inspirations/expirations cycles per minute);

time counting means: clock 6a (threshold value: 6 hours);

patient signal means 9: when one of the threshold values of oximeter sensor 6c, respiratory rate 6b, or clock 6a are in favor of a re-administration of sufentanil, light 9a emits a light on device 1.

Accordingly, the patient will know what will be administered upon activation of control means 8. The patient may then make a decision whether or not to activate control means 8.

Course of therapy:
at T=0, the patient, without any medical facility, actuates control means 8 of the device 1 for the first time: the patient administers active formulation 12.

at T=3 hours, the patient introduces nosepiece 7a of device 1 into one nostril. After about 20 seconds, light 9a emits alight indicating that the clock (and potentially the biological parameters) prohibits the administration of active formulation 12: the patient has the choice of whether or not to administer active formulation 11.

at T=6.1 hours, the patient introduces nosepiece 7a of device 1 into one nostril. After about 20 seconds, light 9a emits a light, indicating that at least one of its two biological parameters (oxygen saturation and respiratory rate) prohibits the administration of active formulation 12: the patient has the choice of whether or not to administer active formulation 11.

A T=8 hours, the patient introduces nosepiece 7a of device 1 into one nostril. After about 20 seconds, light 9a remains off: the patient may administer active formulation 12.

What is claimed:
1. A method for sequential intranasal administration of at least one active ingredient selected from a DR group having at least one side effect of respiratory depression and at least one active ingredient selected from an ADR group that counteracts respiratory depression that may he induced by the at least one active ingredient of the DR group, the method comprising:

administering, from a first storage space, an initial dose of a first active formulation comprising the at least one active ingredient selected from the DR group, in response to an initial actuation of a portable sequential intranasal administration medical device by a patient wishing to receive pharmaceutical administration; and after administering the initial dose, administering, from at least a second storage space, at least one subsequent dose of a second active formulation different from the first active formulation comprising the at least one active ingredient selected from the ADR group without administering the first active formulation, in response to at least one subsequent actuation of the portable sequential intranasal administration medical device by the patient wishing to receive subsequent pharmaceutical administration.

2. The method for sequential intranasal administration of claim 1, wherein the first active formulation further comprises at least one active ingredient from the ADR group.

3. The method for sequential intranasal administration of claim 2, wherein the at least one active ingredient from the ADR group of the first active formulation is identical to the at least one active ingredient from the ADR group of the second active formulation.

4. The method for sequential intranasal administration of claim 1, wherein the portable sequential intranasal administration medical device comprises at least one device for measuring at least one of time or at least one biological parameter, the method further comprising measuring at least one of time or at least one biological parameter via the at least one device, wherein administering the at least one subsequent dose is based on the measured time and/or the at least one biological parameter.

5. The method for sequential intranasal administration of claim 4, wherein the at least one device for measuring at least one of time or at least one biological parameter is configured to measure at least one of oxygen saturation or respiratory rate.

6. The method for sequential intranasal administration of claim 1, wherein the second active formulation further comprises at least one active ingredient from the DR group.

7. The method for sequential intranasal administration of claim 6, wherein the at least, one active ingredient from the DR group of the second active formulation is identical to the at least one active ingredient from the DR group of the first active formulation.

8. The method for sequential intranasal administration of claim 1, wherein the at least one active ingredient from the DR group is selected from a group consisting of benzodiazepines and the least one active ingredient from the ADR group is flumazenil.

9. The method for sequential intranasal administration of claim 1, wherein the at least one active ingredient from the DR group is sufentanil and the at least one active ingredient from the ADR group is naloxone.

10. The method for sequential intranasal administration of claim 1, wherein the at least one active ingredient from the DR group is selected from a group consisting of opioid agonists and the at least one active ingredient from the ADR group is selected from a group consisting of opioid antagonists.

* * * * *